(12) United States Patent
Emminger

(10) Patent No.: US 11,274,272 B2
(45) Date of Patent: Mar. 15, 2022

(54) METHOD FOR A PHOTOCHEMICAL PROCESS, SUCH AS A PHOTOCATALYTIC AND/OR PHOTOSYNTHETIC PROCESS

(71) Applicant: Beco Invest B.V., Houten (NL)

(72) Inventor: Franz Emminger, Hainburg (AT)

(73) Assignee: BECO INVEST B.V., Houten (NL)

( * ) Notice: Subject to any disclaimer, the term of this patent is extended or adjusted under 35 U.S.C. 154(b) by 287 days.

(21) Appl. No.: 15/314,674

(22) PCT Filed: May 27, 2015

(86) PCT No.: PCT/AT2015/000081
§ 371 (c)(1),
(2) Date: Nov. 29, 2016

(87) PCT Pub. No.: WO2015/179888
PCT Pub. Date: Dec. 3, 2015

(65) Prior Publication Data
US 2017/0130181 A1    May 11, 2017

(30) Foreign Application Priority Data
May 30, 2014 (AT) .................................. A 431/2014

(51) Int. Cl.
*C12M 1/00* (2006.01)
*C12M 1/12* (2006.01)
*C12M 1/02* (2006.01)
*C12M 1/34* (2006.01)

(52) U.S. Cl.
CPC ............ *C12M 21/02* (2013.01); *C12M 23/06* (2013.01); *C12M 23/22* (2013.01); *C12M 27/00* (2013.01); *C12M 27/20* (2013.01); *C12M 29/20* (2013.01); *C12M 41/44* (2013.01)

(58) Field of Classification Search
None
See application file for complete search history.

(56) References Cited

U.S. PATENT DOCUMENTS

| 5,091,315 A | 2/1992 | McCarty et al. | |
| 2005/0239182 A1* | 10/2005 | Berzin | C12M 21/02 435/166 |
| 2009/0137031 A1 | 5/2009 | Hirabayashi | |
| 2011/0027875 A1* | 2/2011 | Cathcart | C12M 21/02 435/292.1 |
| 2012/0003734 A1 | 1/2012 | Mohr | |
| 2012/0021498 A1* | 1/2012 | Muller-Feuga | C12M 21/02 435/257.1 |

FOREIGN PATENT DOCUMENTS

| AT | 506373 | 8/2009 | |
| AT | 507989 | 9/2010 | |
| DE | 4134813 | 4/1993 | |
| DE | 4139134 | 4/1993 | |
| DE | 19507149 | 9/1995 | |
| DE | 19644992 | 3/1998 | |
| EP | 738686 | 10/1996 | |
| GB | 2235210 | 2/1991 | |
| WO | 98/18903 | 5/1998 | |
| WO | 2009/051478 | 4/2009 | |
| WO | WO-2009051478 A2 * | 4/2009 | ............ C12M 21/02 |

OTHER PUBLICATIONS

PCT Search Report in PCT/AT2015/000081.
Austrian Search Report in A 152/2008.
Written Opinion in PCT/AT2015/000081.

* cited by examiner

*Primary Examiner* — Soren Harward
*Assistant Examiner* — Paul D Pyla
(74) *Attorney, Agent, or Firm* — Maier & Maier, PLLC

(57) ABSTRACT

The invention relates to a method for a photochemical process, such as a photocatalytic and/or photosynthetic process, in particular for the culture and production or the hydroculture of microorganisms. A reaction medium (6) is conducted in a meandering manner in a reactor element (2) which is made of at least two upright and connected pipes (3) or chambers (13). Multiple reactor elements (2) are serially connected into a bio solar reactor (1), and a reaction medium (6) flow which is stress-free for the microorganisms is generated in the bio solar reactor (1) using hydrostatic pressure and level compensation. Inlet and outlet openings (4, 5) are arranged on the lower face (8) of each individual reactor element (2) on each of the outermost pipes (3) or chambers (13). The reaction medium (6) flows around all of the connections in the lower region, in particular the inlet opening (4), the outlet opening (5), and the introduction inlet (17). The invention also relates to a device for carrying out the method and to a bio solar reactor.

19 Claims, 3 Drawing Sheets

Figure 2:
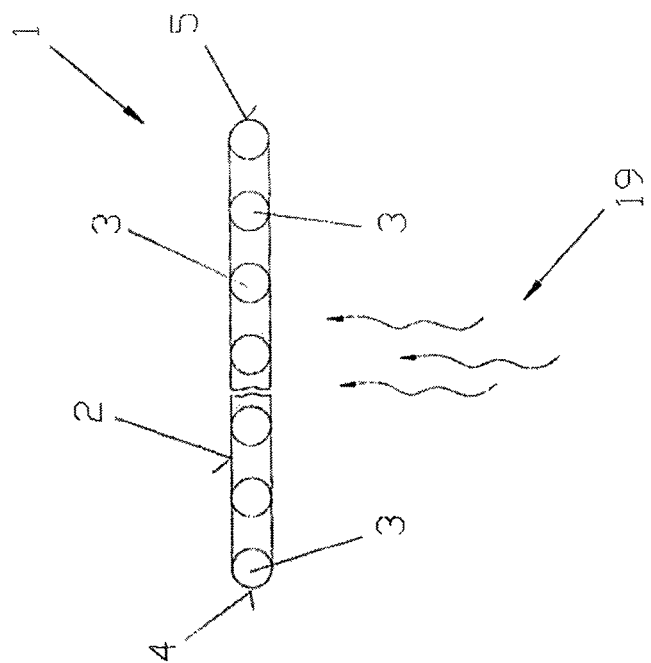

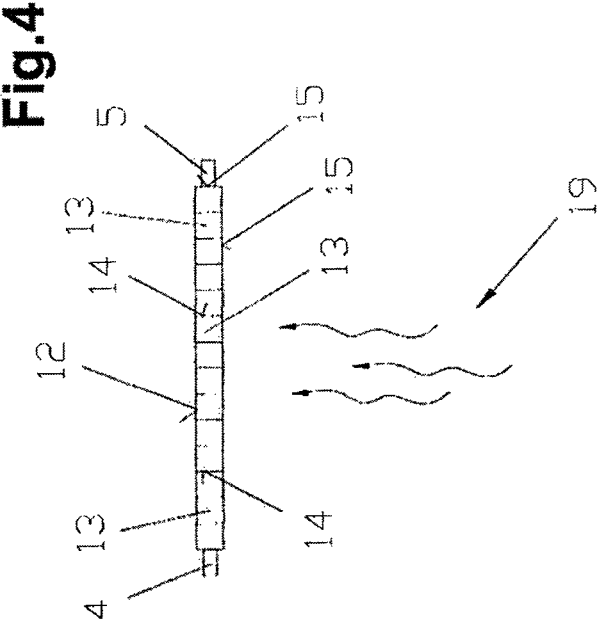
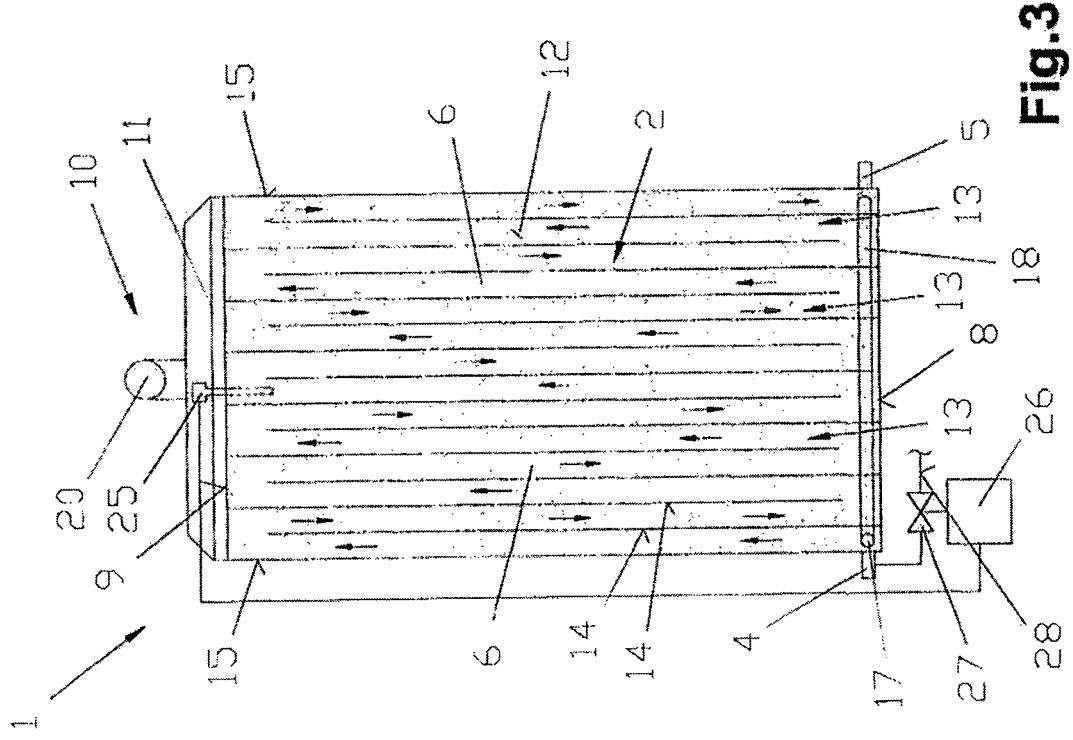

METHOD FOR A PHOTOCHEMICAL PROCESS, SUCH AS A PHOTOCATALYTIC AND/OR PHOTOSYNTHETIC PROCESS

The invention relates to a method for a photochemical process, such as a photocatalytic and/or photosynthetic process, in particular for the culture and production or the hydroculture of, preferably phototropic, microorganisms, wherein a reaction medium, for instance, an aqueous solution or a suspension of microorganisms and nutrient solution, is conducted in a meandering manner in a reactor element which is made of at least two upright and connected pipes or chambers, wherein the conducting of the reaction medium in a meandering manner is performed perpendicularly or possibly inclined at an angle to the sun, and preferably multiple reactor elements are serially connected into a bio solar reactor, and a reaction medium flow which is stress-free for the microorganisms is generated in the bio solar reactor using hydrostatic pressure and level compensation. The invention also relates to a device for carrying out the method and to a bio solar reactor.

AT 506 373 B1 discloses a system in which the bio solar reactor consists of at least one reactor element, wherein the reactor element is made of at least two upright pipes connected at the bottom so as to achieve a meandering course of a reaction medium. The reaction element comprises an inlet and an outlet on the upper reactor edge. The meandering conduct of the medium is performed perpendicularly, with a stress-free flow for the medium being generated due to the hydrostatic pressure and level compensation.

It is of disadvantage here that with such a system the introduction and the output of the medium takes place on the upper face of the system, so that accessibility is substantially aggravated. In particular when samples are taken for determining the growth of the microorganisms, this has to be done on the upper face with such systems.

Another similar system is known from AT 507 989 B1 and from US 2012/0003734 A1 in which the reactor element is now arranged in a preferably transparent liquid.

DE 41 34 813 A1 discloses a bio reactor for phototropic microorganisms which consists of glass or plastics. The culture medium is either pumped through the bio reactor or is guided downward through the horizontally arranged web plates in a meandering manner. Furthermore, means producing turbulence are arranged in the webs. In correspondence with this method, carbon dioxide is introduced at the top and natural or artificial light is used for operation. The bio reactor is positioned and/or tracked at right angle to the light source.

Furthermore, GB 2 235 210 A and DE 196 44 992 C1 also disclose bio reactors for phototropic microorganisms or for photocatalytic processes, respectively.

EP 738 686 A1 discloses photocatalytic waste water purification in a bio reactor, where the liquid to be purified is guided through multiple web plates of transparent plastics. For temperature regulation translucent commercially available multiple web plates may be used.

Furthermore, WO 98/18903 describes an actively or passively temperature-controllable solar element of multiple web plates with at least three belts. Layers within the reactor are used alternatingly for a photochemical and a photosynthetic process. In a closed reactor with a sealed front face and horizontally arranged web plates the culture medium is conducted downward in a meandering manner.

Moreover, DE 195 07 149 C2 discloses a screw turbine with a trough and a generator for electricity generation. DE 41 39 134 C2 discloses a screw turbine for energy conversion.

Of course, the hydrostatic balance of forces is known as a hydrostatic paradox, also called Pascal's paradox. This is a seeming paradox which describes the phenomenon that a liquid exerts a hydrostatic pressure on the bottom of a vessel as a function of the filling level of the liquid, but that the shape of the vessel has no influence.

Vessels which are open at the top and connected at the bottom are called communicating vessels or communicating pipes. A homogeneous fluid is at equal levels in them since air pressure and gravity act equally on the vessels. In the case of inhomogeneous liquids the liquid columns behave with respect to their height inversely to their specific weight.

Usually—as is also the case in some of the above-mentioned methods—the transport in solar reactors is performed by customary pumping methods. This proceeding causes stress in the reaction medium, be it by high pressure, negative pressure, high acceleration, or crushing. Subjected to this stress, the potential photosynthetic capabilities of most phototropic microorganisms decrease. Cells are destroyed, damaged, and/or the microorganisms take time and/or need metabolites for regeneration before they can fully resume the processes assigned to them. Likewise, subjected to this stress, the potential photocatalytic capabilities of most photochemical processes decrease since molecules are destroyed or damaged and/or take time and/or need further oxidizing agents before they can fully resume the processes assigned to them.

It is an object of the invention to provide a method of the initially quoted kind which avoids the above-mentioned disadvantages, on the one hand, and ensures safe, economically rational operation of the system, on the other hand. Another object of the invention consist in achieving process optimization in the system in industrial operation.

The method for a photochemical process, such as a photocatalytic and/or photosynthetic process, in particular for the culture and production or the hydroculture of, preferably phototropic, microorganisms in accordance with the invention is characterized in that inlet and outlet openings are arranged on the lower face of each individual reactor element on each of the outermost pipes or chambers, wherein a branch ascending against the direction of gravity is assigned to the inlet opening and a branch descending in the direction of gravity is assigned to the outlet opening, and that the reaction medium flows around all of the connections in the lower region, in particular the inlet opening, the outlet opening, and the introduction inlet.

It is of advantage that all connections, in particular the inlet and the outlet, are arranged on the lower face of the module, so that easier handling of problems with the connections is possible. In the state of the art the connections are exclusively arranged on the upper face. Thus, in the case of the configuration of the system in accordance with the invention it is no longer necessary to go up, for instance, 6 meters in height to be able to perform maintenance, taking of samples, or examination activities.

A substantial advantage, however, consists in that the connecting pieces, in particular the inlet opening and the outlet opening, are always flown with liquid, so that the operation of the system was improved substantially since air which may have a detrimental effect on the microorganisms cannot enter. Thus, it is also ensured that the seals used for the connecting pieces are always flown with liquid and hence cannot run dry.

Moreover, the reactor elements are designed such that, when two or more reactor elements are connected together, no pumps, motors or the like are required, so that quick growth of the microorganisms in stress-free flowing of the reaction medium is achieved.

With the invention it is thus possible for the first time to achieve a transport which takes care of the microorganisms, so that damage in the course of their production process is avoided. The reaction medium flows in a meandering manner through the upright interconnected reactor elements. The reactor elements are interconnected such that the inlet and the outlet are now arranged to be easily accessible on the lower face. Throughflow is achieved by utilizing hydrostatic pressure compensation with minimal loss of height within the entire reactor. By the largely pressure-free and appression-free transport of the reaction medium in a bio solar reactor the reaction process is impaired as little as possible.

The method according to the invention may, for instance, be used for the following fields of application:

- The photocatalytic purification of waste water
- The photosynthetic metabolization of $CO_2$ to oxygen, by phototropic microorganisms
- Culture and production of phototropic microorganisms for research purposes
- Research in photochemical and/or photosynthetic processes
- Culture and production of phototropic microorganisms for food products and base food substances
- Culture and production of phototropic microorganisms for base substances of pharmaceutical industry
- Culture and production of phototropic microorganisms for fuels and base substances for fuel production and energy production
- Culture and production of phototropic microorganisms for base substances of chemical industry
- Culture and production of phototropic microorganisms outputting usable gases, such as hydrogen, in the photosynthetic process Due to the utilization of hydrostatic power compensation while the reaction medium flows through the reactor elements a quasi stress-free transport of the possibly entrained microorganisms takes place. Furthermore, it is possible to achieve energy optimization, defined distribution of light, space optimization, supply with additives, defined temperature regulation, specified control, and improved gas output.

In accordance with a further particular feature of the invention a continuous or batch-wise introduction of liquid and/or gaseous additives, such as in particular nutrient solutions and/or oxidizing agents and/or active ingredients and/or dissolved substances promoting the process, is performed, preferably during the process, on the lower face in the region of the inlet and/or outlet openings of the reaction medium, wherein the introduction of the additives on the lower face of the liquid column causes mixing and regular distribution of the additives in the reaction medium. Thus, controlled and optimized introduction of nutrient solutions and solutions promoting the process as well as controlled and optimized introduction of nutrient and process gases are possible. Any interventions in the reaction medium take place on the lower face of the reaction elements.

In accordance with a further feature of the invention the filling level of the reaction medium is detected by a filling level control provided preferably on the upper face of the reactor element, and is kept on a predeterminable value by adding a liquid and/or the reaction medium in the case of falling. This ensures an optimum process in correspondence with the visions illustrated above.

In accordance with a further particular feature of the invention the output of gaseous process products, such as for instance oxygen or $CO_2$, is, preferably during the process, performed through the surface of the reaction medium and is preferably transported off or sucked off through an exhaust system on the upper face of the reactor element. This makes it possible to achieve a controlled and optimized reduction of harmful substances, wherein this optimized output also allows the collecting of gaseous process products. The sucking off of the gases results in a safe operation of the system since no toxic gases whatsoever can occur in the area of the system.

In accordance with a further embodiment of the invention the reactor element is closed on the upper face by a closure element which is preferably detachable. This prevents overflowing of the reactor element. At the same time gases are prevented from exiting from the system, in particular the reactor elements.

It is further an object of the invention to provide a device for carrying out the method. It is in particular an object of the invention to improve accessibility of the system in industrial operation.

The device for carrying out the method according to the invention, wherein a reactor, in particular a bio solar reactor, consists of at least one reactor element which is made of at least two upright and connected pipes or chambers, is characterized in that each individual reactor element comprises inlet and outlet openings on the lower face on each of the outermost pipes or chambers, wherein a branch ascending against the direction of gravity is assigned to the inlet opening and a branch descending in the direction of gravity is assigned to the outlet opening, that the reaction medium flows around all of the connections in the lower region, in particular the inlet opening, the outlet opening, and the introduction inlet, and that preferably the inlet and/or outlet opening is arranged at the deepest position of the reactor element.

Such a device in accordance with the invention has the advantage that the construction can be adapted to the respective phototropic microorganisms or photochemical requirements and the optimum residence time within the entire reactor in correspondence with the process result can be influenced by the following parameters:

- Rate of flow
- Cross-section of the reactor elements
- Height of the reactor elements
- Number and property of the introduced, non-gaseous substances
- Property, number, density, and pressure of the blown-in gases
- Number of reactor elements connected in meandering conduct
- Possibility of outputting process waste gases
- Process temperatures
- Residence time and position with respect to the light
- Residence time in maturation tanks or dark tanks In accordance with an alternative design of the invention the reactor element is formed of multiple, in particular seventy, preferably rectangular, upright chamber or pipes which are separated from each other by a separating wall, wherein the separating wall is open once on the upper face and subsequently on the lower face, i.e. in the region of a bottom, for circulation of the reaction medium. The advantage consists in that this increases the stability of the reactor elements since the individual chambers adjoin each other without a gap.

The reactor, in particular the bio reactor, may consist of transparent, translucent, coated, and uncoated materials. Likewise, the pipes or web plates could consist of glass or light or UV light-permeable plastics such as, for instance, polymethyl methacrylate. The reactor elements may be designed both of commercially available and possibly processed, and of separately manufactured components meeting the above requirements.

The reactor elements are arranged such that continuous flowing in a meandering manner from the bottom to the top and from the top to the bottom is ensured. The inflow in and the outflow from the reactor are positioned in the lower region.

After entering the reactor, the reaction medium, utilizing hydrostatic power compensation, flows stress-free through the entire reactor in upright meanders. Upon arrival in the last reactor element the reaction medium leaves the hydrostatic bio reactor and is conducted pressure-free or pressureless to a maturation tank or a collection container or a further reactor. From the collection container the reaction medium may be finished or be supplied stress-free to an intermediate storage or to further processing.

Due to the fact that the inlet and/or outlet opening is arranged at the deepest position of the reactor element, regular flowing of the reactor liquid through of the reactor is ensured.

In accordance with a particular feature of the invention, in a connection of two or more reactor elements a respective outlet opening is always connected with a respective inlet opening, preferably by a connecting line. This makes the system extendable at will.

In accordance with a further particular feature of the invention, for the continuous or batch-like introduction of additives, such as for instance nutrient solutions or nutrient gases and/or oxidizing agents and/or active ingredients and/or dissolved substances or gases promoting the process, preferably during the process, on the lower face of the reactor, in the region of the deflection of the reaction medium and/or through the connecting line, at least one introduction inlet is provided. The reaction medium may optionally be enriched with substances dissolved in liquids and meeting the requirements of the microorganisms or the requirements of the process before entering the reactor and/or be supplied with fluid nutrients or oxidizing agents while flowing through the reactor.

The nutrient content in the reaction medium which decreases in the photosynthetic process due to the continuous growing up of the microorganisms may be balanced by the continuous and/or clocked introduction of a nutrient solution.

The degree of efficiency in the reaction medium which decreases in the photochemical process due to continuous reacting may also be balanced by the continuous and/or clocked introduction of further effective substances.

For the introduction of the fluid nutrients or oxidizing agents a possibility of supply is provided via controllable valves on the lower face of the reactor elements. Due to the conduct of the reaction medium in a meandering manner and/or due to the ascending fluid substances, such as the gas bubbles, good mixing and distribution within the entire reactor is provided. Of course, gaseous nutrients, oxidizing agents or substances may also be introduced in this manner.

The introduced gases cause, by the ascending of the gas bubbles, self-purification of the inner face of the reactor. The sampling location for taking samples to examine the progress of the process is also provided at the bottom of the reactor element.

In accordance with a further particular feature of the invention the reactor elements are closed on the upper face with a, preferably detachable, closure element, and for the output of gaseous process products, such as for instance oxygen or $CO_2$, preferably during the process, an exhaust system is provided which is provided above the surface of the reaction medium or above the upper face of the reactor elements, respectively. As the case may be, a collecting device is provided with the exhaust system above the surface of the reaction medium or above the upper face of the reactor elements, respectively, for outputting gaseous process products. Gaseous process products such as metabolites which are produced in the photosynthetic or photochemical process can, due to the absence of pressure in the reactor element, ascend freely in the reaction medium.

Oxygen which is produced in the photosynthetic process and which damages phototropic microorganisms, and process waste gases which are produced in the photochemical process can, due to the absence of pressure in the reactor element, ascend freely in the reaction medium. Due to the construction of the reactor element which is completely or partially open to the top, evading and/or sucking off of the oxygen is possible.

The outputting of process waste gas is promoted by ascending bubbles produced in the process and/or is possibly controlled by additionally blown-in gases.

For outputting gaseous process products a collecting device is provided with the exhaust system above the surface of the reaction medium or above the upper face of the reactor elements, respectively. Thus, the gaseous process products can be collected and possibly be further used or be disposed of. Loss of reaction medium by evaporation and/or by spraying loss and a controlled discharging and collecting of gases is also possible by a closed construction.

Before the inlet, in particular before the inlet opening, and/or after the outlet, in particular after the outlet opening, a siphon may be provided. The reaction medium may be supplied through a siphon to the first reactor element in a pressure-free or pressure-less manner, and may be discharged through a further siphon after the reactor in a pressure-less and possibly gas-tight manner.

In accordance with a particular feature of the invention at least one filling level sensor is arranged preferably on the upper face of the bio solar reactor, wherein the filling level sensor is connected with a refill system. Thus, the filling level of the reaction medium is always kept at its predefined value. An optimum process is thus ensured.

In accordance with a particular further development of the invention the reactor is adjustable with respect to light radiation via at least one axis. Since phototropic microorganisms run through an optimum photosynthetic process only in the zone close to the surface and their food intake and division are impaired by too much UV radiation, it is of advantage that they are conducted both to the outer zone and to the interior within the reactor element.

Too intensive, directly irradiating UV light damages or impairs the growth of the microorganisms and increases the temperature of the reaction medium beyond the ideal measure, which has to be cooled again. By the mixing of the reaction medium all phototropic microorganisms get sufficiently to the light zone of the reactor element which is flooded by light and is close to the outer wall. In the case of photocatalytic oxidation it is also of advantage if all molecules within the reactor element are conducted to the light zone of the reactor element which is flooded by light and is close to the outer wall.

Parallel positioning with respect to the light source or parallel following of the solar radiation with the reactor will usually suffice, and thus a massively improved utilization of space becomes possible.

Furthermore, light that is irradiated in parallel is partially reflected by the reactor surface and is available for the opposite reactor. In particular in the case of perpendicular solar radiation, bad geographic location, or phototropic microorganisms which are in need of much light, or photocatalytic processes, a position of the reactor facing the light source at any angle may be chosen.

Another object of the invention consists in providing a bio solar reactor for a process-optimized system in industrial operation.

The object of the invention is solved by the bio solar reactor illustrated in the following.

The bio solar reactor in accordance with the invention is characterized in that each individual reactor element comprises inlet and outlet openings which are arranged on the lower face on each of the outermost pipes or chambers, wherein a branch ascending against the direction of gravity is assigned to the inlet opening and a branch descending in the direction of gravity is assigned to the outlet opening, that the reaction medium flows around all of the connections, in particular the inlet opening, the outlet opening, and the introduction inlet, that preferably the inlet and outlet openings are arranged preferably at the deepest position of the reactor element, in particular at the pipes or chambers, and that possibly an exhaust system is arranged on the upper face of the reactor elements.

A design in which the inlet and outlet openings are preferably arranged on the front face of the reactor element, in particular at the pipes or chambers, is of advantage. Thus, a simple construction is achieved and the lines can be laid correspondingly safely.

In accordance with an advantageous design of the invention the individual chambers or pipes are connected into a meandering course, wherein the separating walls arranged between the chambers or pipes are of correspondingly shortened design. Thus, it is achieved in an advantageous manner that the path for the transport of liquid from the inlet to the outlet is substantially extended, such that the reaction medium remains for a sufficiently long time in the reactor to achieve optimum growth.

In accordance with a particular design multiple reactor elements are connected into a reactor panel by a holder. This ensures optimum utilization of the system.

The invention will be explained in more detail by means of embodiments which are illustrated in the drawing.

Figure 1:
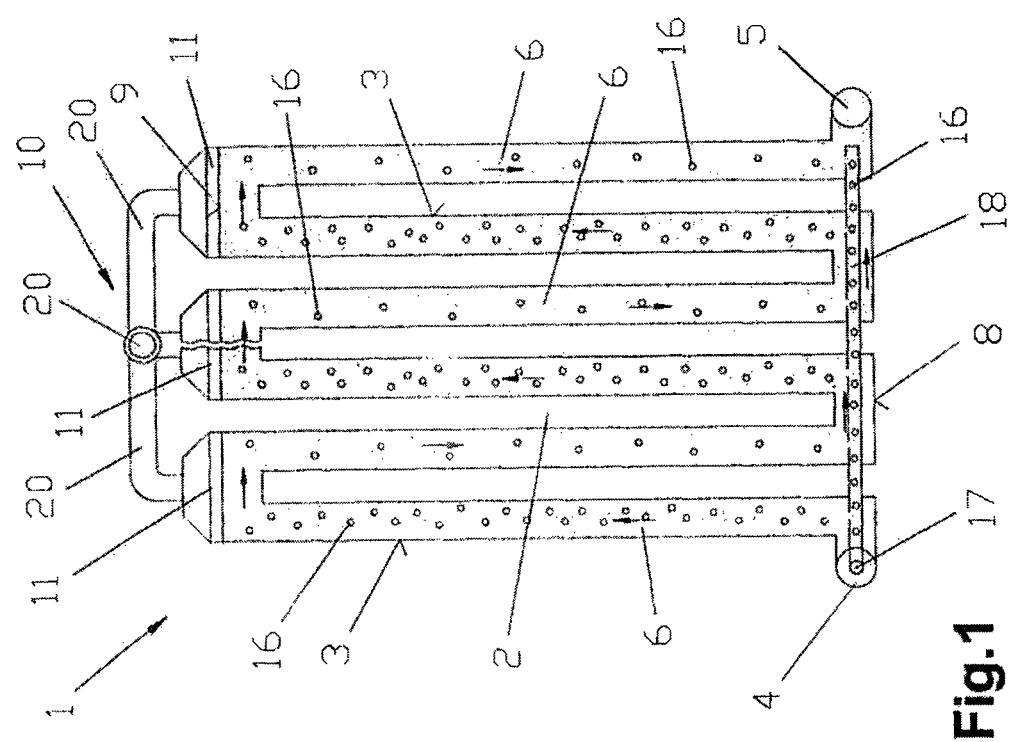
Figure 6:
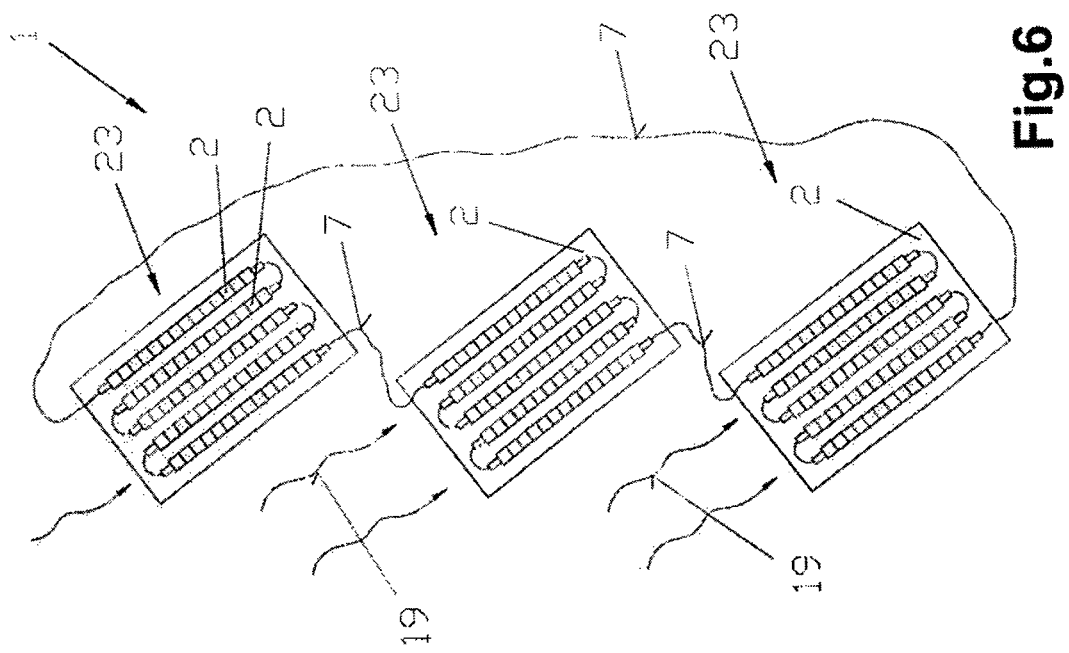
Figure 5:
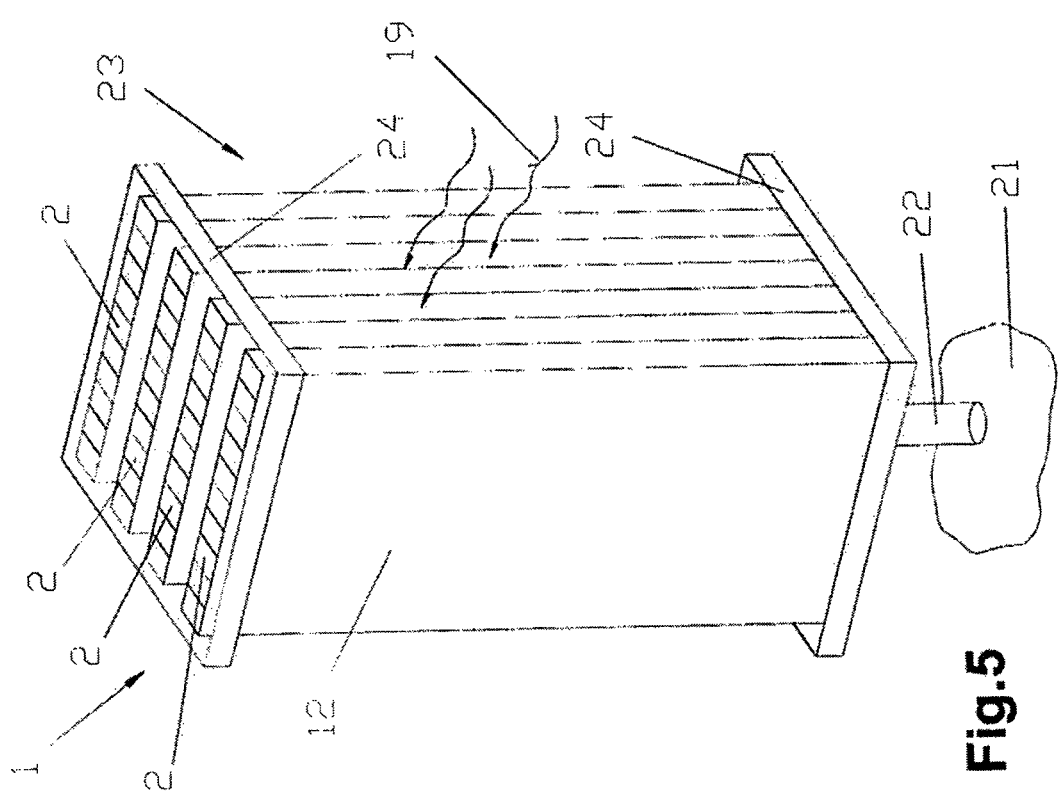

There show:

FIG. 1 a schematic representation of a bio solar reactor consisting of pipes, FIG. 2 a plan view in accordance with FIG. 1, FIG. 3 a schematic representation of a further bio solar reactor consisting of web plates, FIG. 4 a plan view in accordance with FIG. 3, FIG. 5 a schematic representation of a side view of a system with a bio solar reactor, FIG. 6 a schematic representation in plan view of a system in which multiple bio solar reactors are connected together.

In accordance with FIGS. 1 and 2 a reactor, in particular a bio solar reactor 1, consists of at least one reactor element 2 which is made of at least two upright pipes 3 which are connected at the bottom and at the top. For the construction of a reactor element 2 a plurality of pipes 3 are connected in series. Preferably, seventy pipes 3 are joined for forming a reactor element 2, wherein a meandering course through the pipes 3 is formed, i.e. that a respective ascending branch alternates with a respective descending branch and that a passage to the further pipe 3 exists on the lower face and the upper face. On each of the first and last pipes 3 an inlet opening 4 and an outlet opening 5 are arranged at the side of the horizontally positioned pipes 3 which is assigned to the installation surface. At the same time, for forming the bio solar reactor 1, multiple reactor elements 2 are connected consecutively in series or interconnected, respectively, as is illustrated schematically in the following in FIG. 6. It is possible that all reactor elements 2 are of equal design, or else that one or several reactor elements 2 are of different designs, in particular with respect to the number of pipes 3 arranged, i.e. that, for instance, the first reactor element 2 is constructed with 50 pipes 3 and the further reactor element(s) 2 arranged behind in parallel have, for instance, 52, 54, etc. pipes 3.

Such a bio solar reactor 1 is used for a method for a photochemical process, such as a photocatalytic and/or photosynthetic process, in particular for the culture and production or the hydroculture of, preferably phototropic, microorganisms. For operation the bio solar reactor 1 is filled with a reaction medium 6, for example an aqueous solution or a suspension of microorganisms and nutrient solution. In operation the bio solar reactor 1 is supplied through its first inlet opening 4. The conduct or flowing direction of the reaction medium 6 takes place vertically once from the bottom to the top, i.e. against the direction of gravity, and from the top to the bottom, i.e. in the direction of gravity in the reactor element 2, i.e. in a meandering manner through the individual pipes 3 of a reactor element 2. If multiple interconnected reactor elements 2 are connected consecutively, the reaction medium 6 flows in a meandering manner through the reactor elements 2 and exits from the outlet opening 5 at the last pipe 3 of the reactor element 2 and is connected with the inlet opening 4 of the next reactor element 2 by a connecting line 7, as illustrated in FIG. 6. Both the introduction or supply and the outputting of the reaction medium 6 to/from the bio solar reactor 1 is preferably performed continuously, pressure-less and free to the atmosphere. It is also possible that an own filling aperture (not illustrated) may exist, or that filling is performed through one of the inlet openings 4. The inlet opening 4 and the outlet opening 5 are always arranged on the lower face 8 of a pipe 3 for better handling, whereas a filling aperture is arranged in parallel to the inlet opening 4 or on the upper face 9. If the system is constructed as a closed system, it is necessary during filling that a vent hole or an exhaust system 10 is arranged from which the air or gases contained in the reactor elements 2 can evade or are sucked off. Preferably, the exhaust system 10 is arranged on the upper face 9 since the air ascends in the reaction medium 6 and may thus evade easily to the top.

The reactor elements 2 are thus connected with one another in a meandering manner as communicating pipes 3, wherein the inlet opening 4 and the outlet opening 5 are always positioned or arranged on the lower face 8 of the reactor elements 2, in particular the side facing the installation surface. The reactor elements 2 are closed on the upper face 9 by a closure element 11, wherein the closure element 11 is designed detachable so as to enable easy cleaning of the system, for instance.

Utilizing the hydrostatic pressure and level compensation, a flow of the reaction medium 6 is produced at the inlet opening 4 through the feeding of the reaction medium 6, i.e. the individual reactor elements 2 comprise inlet 4 and outlet openings 5 which are arranged on the lower face 8 on the outermost pipes 3, wherein a branch against the direction of gravity, i.e. an ascending branch, is assigned to the inlet opening 4 and a branch in the direction of gravity, i.e. a descending branch, is assigned to the outlet opening 5, and that the exhaust system 10 is arranged on the opposite upper face 9 of the reactor elements 2, so that ascending gases may evade or be sucked off through the exhaust system 10. For the method this means that a stress-free flow of the reaction medium 6 without pumping devices is generated for the microorganisms, so that damages of the reaction medium 6, especially of the algae contained therein, cannot occur and the yield of such a system is considerably increased. This enables free flowing between the individual reactor elements 2 without further energy having to be supplied.

In accordance with FIGS. 3 and 4 an alternative construction of a bio solar reactor 1 is illustrated. This bio solar reactor 1 consists of web plates or multiple web plates 12. In this construction a reactor element 2 consists of at least two, preferably rectangular, upright chambers 13 formed of the web or multiple web plates 12, wherein one side of the chamber 8 is designed as a separating wall 14. Both the inlet opening 4 for the introduction or feeding and the outlet opening 5 are provided on the lower outermost reactor edge, in particular at the front faces of the multiple web plates 12, i.e. that the chambers 13 correspond to the pipes 3, and that a reactor element 2 and/or the web plate or multiple web plate 12 is formed by consecutively arranging multiple chambers 13 or pipes 3, wherein for the bio solar reactor 1 preferably multiple reactor elements 2 are connected in series, as may be seen in FIGS. 5 and 6.

To achieve a meandering course of the chambers 13, when two or more chambers 13 are connected, their separating wall 14 is designed lower with an ascending branch than is the separating wall 14 between the pipes 3 or chambers 13 with a descending branch, i.e. that in an ascending branch the separating wall 14 is shortened on the upper face 9 with respect to the outer wall members 15 of the chamber 13 whereas with a descending branch the separating wall 14 is designed shorter on the lower face 8, i.e. the outer wall members 15 of the chamber 13. This produces an overflow or a communicating aperture, respectively, if the liquid level in the reactor elements 2 is higher than the separating wall 14 between the reactor elements 2. Energy consumption is minimized in that pumps between the process steps are largely renounced and any number of identical or different process steps may be coupled to one another in the same height of throughflow.

The individual reactor elements 2 are preferably transparent or translucent or, if necessary, also lightproof. Both glass or UV-permeable plastics, such as polymethyl methacrylate, may be used as materials. The connections of one reactor element 2 to another reactor element 2 are now positioned on the lower face 8 of the plate, in particular of the web plate or multiple web plate 12 of the reactor element 2. The inlet opening 4 and the outlet opening 5 are designed and milled out such that the inlet openings 4 and outlet openings 5 for pipe connectors or connecting lines 7, respectively, to the next reactor element 2 are respectively arranged on the lower face 8 of the outermost chamber 13. The chamber 13 at the liquid inlet, i.e. with the inlet opening 4, is an ascending branch in which the reaction medium 6 flows against the direction of gravity to the upper face 9 whereas the chamber 13 at the outlet, i.e. at the outlet opening 5, is a descending branch in which the reaction medium 6 flows from the upper face 9 to the lower face 8 in the direction of gravity.

The filling and the operation of the bio solar reactor 1 are carried out in analogy to the explanations with respect to FIGS. 1 and 2. For instance, the reaction medium 6 is first of all filled stress-free into the bio solar reactor 1 with a filling pipe in that the reaction medium 6 is, from a storage container (not illustrated) which is positioned above the level of the upper face 9 of the bio solar reactor 1, conducted from the storage container through the filling pipe to the lower inlet opening 4, so that the reaction medium 6 may flow into the reactor elements 2 without pumps and hence without damages. Basically, it is, however, also possible that a pump is used in the filling process and that the flowing of the reactor is subsequently performed without a pump.

With respect to the light radiation on the reactor elements 2—which will be dealt with later—a tilted reactor (not illustrated) is possible. Despite the fact that the reactor is tilted at an angle, the reaction medium 6 flows once from the top to the bottom or in the direction of gravity, respectively, and from the bottom to the top or against the direction of gravity, respectively. It is essential that the reactor elements 2 are installed vertically or at an angle which is slightly oblique to the vertical line, wherein the reactor elements 2 have a length of between 15 and 30 m, in particular 19 m, and the breadth of the reactor elements 2 is determined on the basis of the size of chamber 13 or the pipes 3 and the number thereof. Preferably, 70 chambers 13 are arranged side by side. It can thus be said that the reactor elements 2 preferably project 19 meters up, so that appropriate precautions for stabilization are required.

In accordance with the embodiments of FIGS. 1 and 2 and of FIGS. 3 and 4, for the continuous or batch-like introduction of additives 16 (illustrated in FIG. 1), such as for instance nutrient solutions or nutrient gases and/or oxidizing agents and/or active ingredients and/or dissolved substances or gases promoting the process, preferably during the process, on the lower face 8 of the reactor, in the region of the deflection of the reaction medium 6, at least one introduction inlet 17, for instance, a controllable valve, is provided, as is illustrated schematically. It is of course possible that the introduction inlet 17 is combined with the inlet opening 4. The introduction inlet 17 is preferably connected with a supply pipe 18 through which the additives 16 are distributed in the individual chambers 13 or pipes 3.

In correspondence with the method the reaction medium 6 is optionally saturated with $CO_2$ or other gases prior to entering the reactor. The degree of saturation is enriched in correspondence with the requirements of the process and/or supplied with $CO_2$ or other gases while dwelling in the reactor. The $CO_2$ content in the reaction medium 6 which decreases in the photosynthetic process due to continuous growing up of the microorganisms may be balanced by the continuous or clocked introduction of $CO_2$.

By introducing the additives 16 at the lower end of the liquid column through the introduction inlets 17 and the supply pipe 18 in accordance with FIGS. 1 and 3, mixing and regular distribution of the additives 16 in the reaction medium 6 is performed, as is illustrated schematically.

The introduction of additives 16, such as fluids and gases, further optimizes the supply with light since, caused by the turbulence in the reaction medium 6 thus produced, all molecules or phototropic microorganisms are sufficiently conducted to the light zone of the reactor element 2 which is flooded with light and is close to the outer wall—indicated with the arrows 19. The introduction of fluids and gases produces turbulence in the reaction medium 6, so that a further advantage takes effect, namely that a continuous cleaning of the inner faces of the reactor is caused by the rising of the gas bubbles.

Furthermore, by the fluids and gases which are introduced in a defined manner, heating or cooling of the reaction medium 6 may also take place. The introduced additives 16 may thus be used for controlled temperature regulation of the reaction medium 6.

A design of the bio solar reactor 1 with an Archimedean screw (not illustrated) is also possible. The Archimedean screw or a helix pursuant to Da Vinci serves to transport the reaction medium 6 both within the reactor and between reactor parts or reactors. A respective siphon is provided upstream of the inlet and downstream of the outlet. It is to be understood that the siphons may also be arranged independently of the Archimedean screw upstream of the inlet and downstream of the outlet from the reactor. The reaction medium 6 may be supplied pressure-free or pressure-less to the first reactor element 2 through a siphon, wherein this is also possible with the embodiments of FIGS. 1 to 6. The Archimedean screw or a helix pursuant to Da Vinci may be used in the method for continuous photocatalytic and photosynthetic processes and transports in bio solar reactors 1. In particular whenever the transport of the reaction medium 6 requires to overcome differences in height. The use of the Archimedean screw or the helix pursuant to Da Vinci enables a onetime or also a repeated stress-free transport or it may be used for the filling of the system. This device could be used for the following applications:

Transport, for the repeated passage of the reaction medium 6, through the same reactor.

Transport between a series of, possibly different, reactors and/or maturation tanks, which are passed through once or repeatedly.

Onetime or repeated transporting of a reaction medium 6 alternatingly between a tank and an arbitrary bio reactor.

Onetime or repeated transport of a reaction medium between tanks.

To achieve a yield of the system which is as high as possible, a pressure-free or pressure-less transport of the reaction medium 6 is of advantage since this does not destroy or damage the algae or the reaction medium 6, respectively, and the growth is hence not hindered, i.e. the reaction medium 6 is, during the whole transport, not subject to any further pressure than the one occurring within the transport element by the inherent weight of the reaction medium 6. Due to low rotational speed the reaction medium 6 is not subject to any noteworthy centrifugal forces. The development of the microorganisms or the course of the process is not interrupted or disturbed by the transport. The processes may take place free of stress, acceleration and pressure, so that the growth of the algae or microorganisms, respectively, is not interrupted. During the whole transport the reaction medium 6 is not subject to any higher appression than the one produced within the transport element by the free flowing of the reaction medium. The development of the microorganisms or the course of the process is not interrupted or disturbed by the transport. Harms by abrasion and damages of the cellular walls of the microorganisms or molecules such as by pumps are excluded.

Due to the utilization of the hydrostatic pressure compensation in an Archimedean screw or in a helix pursuant to Da Vinci freedom of appression is maintained.

For the output of gaseous process products, such as for instance oxygen, preferably during the process, the exhaust system 10 is provided which is arranged above the surface of the reaction medium or above the upper face 9 of the reactor elements 2, respectively. For the output of these gaseous process products a collecting device 20 with a sucking system (not illustrated) which is arranged above the liquid level of the reaction medium 6 or above the upper face 9 of the reactor elements 2, respectively, may be provided.

In the case of perpendicular solar radiation on the reactor, bad geographic location, or microorganisms which are in need of much light, or photocatalytic processes the bio reactor 1 may be designed to be adjustable with respect to light radiation via at least one axis 22. In a preferred design the bio solar reactor 1 may follow the sun on two axes 22, as is illustrated schematically in FIG. 6 with three reactor elements 2 which are formed of the web plate or multiple web plate 12. The axis 22 may be anchored in the installation face or in the ground 21, respectively.

In accordance with FIGS. 5 and 6 a reactor panel 23 formed of reactor elements 2 is arranged such that the—schematically indicated—light or sun beams 19 impinge in the direction of the panel axis, i.e. on the front side, wherein the reactor panel 23 may follow the sun beams correspondingly. Consequently, the sun beams 19 may enter between the individual reactor elements 2, and hence a very high supply of the microorganisms in the reaction medium 6 with light, in particular the sun beams 19, is ensured. Best possible growth is achieved therewith. It may also be recognized that no aids such as pumps, motors, or the like are used for the transport of liquid within the system. It is, however, possible that preferably so-called impeller pumps are used for the gentle transport of the algae or microorganisms, respectively, in the reaction medium 6. The systems are preferably constructed such that the reactor panels 23 are connected in series, wherein the last reactor panel 23 is in turn connected with the first reactor panel 23 to achieve an endless loop. Thus, the reaction medium 6 may stay in the reactor elements 2 or the reactor panels 23, respectively, until sufficient growth has been achieved.

In accordance with FIG. 6 a plurality of reactor panels 23 which are preferably connected with each other by connecting lines 7 are provided and are arranged such that the light or sun beams 19 run in parallel to the panel axes 22 and may thus again penetrate between the reactor elements 2.

In a specific embodiment variant the reactor elements 2 are mounted in an upper and/or lower holder 24 in an upright hanging and/or standing manner (FIG. 5).

This holder 24 may fulfill the following functions.

The function as a rotating element to follow the sun radiation 19.

The tilting function to tilt the reactor element 2 toward the sun.

Give the reactor elements 2 firm support.

Connect the reactor elements 2 in a meandering manner.

Possibility of closing the individual reactor elements in a gas-tight manner.

This holder 24 may incorporate at least two up to any number of reactor elements 2 into a reactor panel 23. This enables close positioning or consecutive positioning of reactors which enables maximum utilization of space.

The method enables optimum combining of reaction phases with light and rest phases in the dark as well as stress-free transport. Thus, a build-up of processes which are continuously run through once or a modular, controlled, repeated running through of the individual parts is enabled.

Prior to the actual reaction the reaction medium 6 may be basically supplied in an enrichment tank with nutrients and nutrient gases which promote the bio reaction right from the beginning. In the case of waste water purification or removal of pollutants a first enrichment with the respective pollutants which is maximally reasonable for the microorganisms may be generated in the reaction medium.

The reaction medium 6 may be given an ideal temperature and the microorganisms or chemical substances corresponding to the purpose of the reaction may be introduced in a defined amount.

For maintaining the ideal reaction conditions, temperature, content of process fluid, content of process gas, circulation, mixing, supply of light, and discharge of metabolites may be regulated and controlled in the reaction medium 6. Since, in such a closed system, due to the intensive solar radiation 19, vaporization of the liquid, in particular the water content, takes place in the reaction medium 6, it is necessary to permanently monitor the filling level. This is because if the liquid level were to fall below the separating walls 14 on the upper face 9, the flow of the reaction medium 6 would be interrupted and would stop. To prevent this, a filling level sensor 25 which is connected with a liquid supply system 26 is preferably arranged on the upper face 9, as may be seen in FIG. 3. If the reaction medium 6, due to vaporization, falls below a pre-adjustable value, the filling level sensor 25 will detect this and will relay an appropriate signal to the liquid supply system 26. Subsequently, for instance, a valve 27 in the region of the inlet opening 4 is controlled, so that additional liquid, in particular water, or a reaction medium 6, is filled in by a supply line 28. To this end it is merely necessary that the pressure in the supply line 28 is higher than the pressure in the reactor element 2, or that the additional liquid or the additional reaction medium 6 is supplied through a pump.

Since such reactor elements 2 have, for instance, a height of between 5 m and 15 m and the breadth of the reactor element is between 2 m and 2.5 m, a specific filling process is necessary since, due to the meandering course of the liquid, the liquid level may have different height before the filling level sensor 25 indicates the correct filling level. Thus, only a particular amount of additional liquid or reactor medium 6 is filled in, and then it is waited for a defined period until the filling level sensor 25 is examined. It is, of course, also possible that multiple liquid sensors 25 may be arranged per reactor element 2. It is basically possible that refilling through the liquid supply system 26 may be performed from a central place or by several valves 27 of a system. It is essential that, due to the plate construction and the meandering flow direction, it is always taken into account that the filling level does not change immediately across the entire area, but that it is waited for a particular period until a constant rise of the liquid level occurs and hence overflowing may be prevented. The liquid sensor 25 may consist of a simple float or of an electronic sensor which immerses into the reaction medium 6. Also, when the filling level changes, the resistance of the liquid sensor 25 could, for instance, also change. It is also possible that a kind of pressure sensor is used as a liquid sensor 25 on the lower face 8, so that the pressure of the liquid column is monitored.

The above-illustrated method solves the following problems in an advantageous manner:

Continuous photocatalytic and photosynthetic processes and transports in solar reactors Controlled and optimized energy consumption in the process Controlled and optimized introduction of nutrient solutions and solutions promoting the process Controlled and optimized introduction of nutrient gases and process gases Controlled and optimized reduction of pollutants Optimized output and collection of gaseous process products Controlled and optimized supply with light Minimization of space consumption by light guiding Controlled and optimized process temperature Stress-free transport of the reaction medium 6.

It is also possible that the bio solar reactor 1, in particular the reactor elements 2, is/are positioned in a light permeable liquid (not illustrated), i.e. that a light-permeable liquid, such as for instance water, flows around the reactor elements 2.

It is further possible that plates of different construction, in particular reactor elements 2, may be used with such a system. For instance, plates in accordance with AT 506 373 B1 in which all connections are arranged on the upper face 9 may be combined with the plates in accordance with the invention in which all connections are arranged on the lower face 8. For this purpose, however, a pump could be used for conveying the reaction medium 6. Again an impeller pump will be used as a pump for the gentle transport of the microorganisms or algae, respectively, in the reaction medium 6.

Basically it has to be mentioned that, for generating a flow of the reaction medium 6, a pump—not illustrated—may be used. In such a device in accordance with the invention a bio solar reactor 1, in particular a reactor panel 23, preferably of 12 plates, is formed, wherein a plate, for instance, has a height of approx. 6 m and a breadth of approx. 2.10 m, wherein the reaction medium 6 takes approx. 44 hours to flow through all of the plates or reactor elements 2, respectively.

The invention claimed is:

1. A method of culturing phototropic microorganisms in a reaction medium in a bioreactor, wherein the bioreactor comprises at least one reactor element, wherein the reactor element comprises an inlet for the reaction medium from outside of the reactor element, an outlet for the reaction medium to outside of the reactor element, and at least two pipes or chambers for the reaction medium, wherein the at least two pipes or chambers are oriented upright, parallel and fluidly connected to each other, and wherein a first pipe or chamber of the at least two pipes or chambers has the inlet and a second pipe or chamber of the at least two pipes or chambers has the outlet, and wherein the inlet and the outlet are arranged on or close to a lower face of the reactor element, said method comprising:

conducting the reaction medium containing the phototrophic microorganisms in an up and down meandering manner through the at least two upright and parallel pipes or chambers, such that one pipe or chamber has a reaction medium flow against the direction of gravity and with a first fill level, and an adjacent other pipe or chamber has a reaction medium flow in the direction of gravity and with a second fill level that is the same as the first fill level, wherein the reaction medium flows occur one after the other in the meandering manner through the at least two pipes or chambers and such that an entirety of an inner surface of the inlet and an entirety of an inner surface of the outlet come into contact with the reaction medium during said conducting;

exposing, during the conducting, at least a portion of the phototrophic microorganisms to an amount of light sufficient for growth of the portion of the phototrophic microorganisms; and introducing, into the reaction medium during the conducting, at least one of a liquid additive and a gaseous additive at or close to a lower face of the reactor element and into lower ends of each of the first and second pipes or chambers, wherein, during the introducing, the liquid or gaseous additive is:

introduced into the first pipe or chamber at a location adjacent to the inlet and flows in a same upward flow direction as the reaction medium from a bottom of the first pipe or chamber to the first fill level; and introduced into the second pipe or chamber at a location adjacent to the outlet and flows in an upward flow direction while the reaction medium flows from the second fill level toward a bottom of the second pipe or chamber.

2. The method of claim 1, further comprising, during the conducting:

detecting a filling level of the reaction medium in the reactor element with a filling level control; and maintaining the filling level at a predetermined value, wherein a liquid is added to the reaction medium if a fall of the filling level is detected.

3. The method of claim 1, further comprising, during said conducting:

transporting a gaseous product produced by the phototrophic microorganisms in the reaction medium via an exhaust system out of the reactor element, wherein the gaseous product traverses a surface of the reaction medium in the reactor element, and wherein the exhaust system is on or close to an upper face of the reactor element.

4. The method of claim 1, wherein said introducing comprises introducing gas bubbles.

5. The method of claim 1, wherein the at least one reactor element comprises first and second reactor elements, wherein an outlet of the first reactor element is fluidly connected to an inlet of the second reactor element.

6. The method of claim 1, wherein said at least two pipes or chambers are substantially translucent or transparent.

7. The method of claim 1, wherein said at least two pipes or chambers comprise a glass material.

8. The method of claim 4, wherein said at least two pipes or chambers comprise a glass material.

9. A method of culturing phototropic microorganisms in a reaction medium in a bioreactor, wherein the bioreactor comprises a reactor element having an inlet open to an outside, an outlet open to an outside, and first and second pipes or elongate chambers oriented upright, arranged parallel to one another and fluidly connected to each other, wherein the inlet is coupled to a lower end of the first pipe or elongate chamber and the outlet is coupled to a lower end of the second pipe or elongate chamber, said method comprising:

conducting the reaction medium containing the phototrophic microorganisms in an up and down meandering manner through plural pipes or elongate chambers located between the first and second pipes or elongate chambers, such that one pipe or elongate chamber has a reaction medium flow against the direction of gravity and with a first fill level, and another adjacent pipe or elongate chamber has a reaction medium flow in the direction of gravity and with a second fill level that is the same as the first fill level, wherein the reaction medium flows occur one after the other in the meandering manner through the first, plural and second pipes or elongate chambers and such that an entirety of an inner surface of the inlet and an entirety of an inner surface of the outlet come into contact with the reaction medium during said conducting;

exposing, during the conducting, at least a portion of the phototrophic microorganisms to an amount of light sufficient for growth of the portion of the phototrophic microorganisms; and introducing into the reaction medium, during the conducting, at least one of a liquid additive and a gaseous additive, said introducing utilizing a supply pipe coupled to lower ends of the first and second pipes or elongate chambers, wherein, during the introducing, the liquid or gaseous additive is:

introduced into the first pipe or elongate chamber at a location adjacent to the inlet and flows in a same upward flow direction as the reaction medium from a bottom of the first pipe or elongate chamber to the first fill level; and introduced into the second pipe or elongate chamber at a location adjacent to the outlet and flows in an upward flow direction while the reaction medium flows from the second fill level toward a bottom of the second pipe or elongate chamber.

10. A method of culturing phototropic microorganisms in a reaction medium in a bioreactor, wherein the bioreactor comprises an inlet, an outlet, and reactor elements, with each reactor element comprising plural pipes or elongate chambers oriented upright, arranged parallel to one another and fluidly connected to each other, wherein the inlet is located at a lower end of the bioreactor and on one side of the bioreactor and the outlet is located at a lower end of the bioreactor and on an opposite side of the bioreactor, said method comprising:

conducting the reaction medium containing the phototrophic microorganisms in an up and down meandering manner through each reactor element, such that each first pipe or elongate chamber has a reaction medium flow against the direction of gravity and a first fill level, and each second pipe or elongate chamber has a reaction medium flow in the direction of gravity and a second fill level that is the same as the first fill level, wherein the reaction medium flows occur with the same fill level and one after the other in the meandering manner through the plural pipes or elongate chambers and such that an entirety of an inner surface of the inlet and an entirety of an inner surface of the outlet come into contact with the reaction medium during said conducting;

exposing, during the conducting, at least a portion of the phototrophic microorganisms to an amount of light sufficient for growth of the portion of the phototrophic microorganisms; and introducing into the reaction medium, via a horizontally arranged common supply pipe coupled to lower ends of each of the first and second pipes or elongate chambers, at least one of a liquid additive and a gaseous additive, wherein, during the introducing, the liquid or gaseous additive is:

introduced into the first pipe or elongate chamber at a location adjacent to the inlet and flows in a same upward flow direction as the reaction medium from a bottom of the first pipe or elongate chamber to the first fill level; and introduced into the second pipe or elongate chamber at a location adjacent to the outlet and flows in an upward flow direction while the reaction medium flows from the second fill level toward a bottom of the second pipe or elongate chamber.

11. The method of claim 10, wherein each reactor element further comprises third, fourth, fifth and sixth pipes or elongate chambers oriented upright, arranged parallel to one another and fluidly connected to each other, wherein the inlet is coupled to a lower end of the first pipe or elongate chamber and the outlet is coupled to a lower end of the sixth supply pipe or elongate chamber.

12. The method of claim 9, wherein the reactor element further comprises third, fourth, fifth and sixth pipes or elongate chambers oriented upright, arranged parallel to one another and fluidly connected to each other, wherein the inlet is coupled to a lower end of the first pipe or elongate chamber and the outlet is coupled to a lower end of the sixth supply pipe or elongate chamber.

13. The method of claim 1, wherein the at least one reactor element further comprises additional pipes or chambers oriented upright, arranged parallel to one another and fluidly connected to each other, wherein the inlet is coupled to a lower end of the first pipe or chamber and the outlet is coupled to a lower end of a last one of the additional pipe or chamber.

14. The method of claim 1, wherein the inlet and the outlet are each located below the first and second fill levels.

15. The method of claim 9, wherein the inlet and the outlet are each located below the first and second fill levels.

16. The method of claim 10, wherein the inlet and the outlet are each located below the first and second fill levels.

17. The method of claim 1, wherein the location adjacent the inlet is located above a lower end of the first pipe or chamber and the location adjacent the outlet is located above a lower end of the second pipe or chamber.

18. The method of claim 9, wherein the location adjacent the inlet is located above a lower end of the first pipe or elongate chamber and the location adjacent the outlet is located above a lower end of the second pipe or elongate chamber.

19. The method of claim 10, wherein the location adjacent the inlet is located above a lower end of the first pipe or elongate chamber and the location adjacent the outlet is located above a lower end of the second pipe or elongate chamber.

\* \* \* \* \*